(12) United States Patent
Nallakrishnan

(10) Patent No.: US 10,449,088 B2
(45) Date of Patent: *Oct. 22, 2019

(54) APPARATUS AND METHOD FOR PHACOEMULSIFICATION

(71) Applicant: Art, Limited, Grand Cayman (KY)

(72) Inventor: Ravi Nallakrishnan, Westmont, IL (US)

(73) Assignee: Art, Limited (KY)

( * ) Notice: Subject to any disclaimer, the term of this patent is extended or adjusted under 35 U.S.C. 154(b) by 611 days.

This patent is subject to a terminal disclaimer.

(21) Appl. No.: 14/625,342

(22) Filed: Feb. 18, 2015

(65) Prior Publication Data
US 2015/0173950 A1 Jun. 25, 2015

Related U.S. Application Data

(63) Continuation of application No. 12/408,715, filed on Mar. 22, 2009, now Pat. No. 8,992,459.
(Continued)

(51) Int. Cl.
*A61F 9/007* (2006.01)
*A61B 17/32* (2006.01)
(Continued)

(52) U.S. Cl.
CPC ...... *A61F 9/00745* (2013.01); *A61F 9/00736* (2013.01); *A61M 1/0039* (2013.01);
(Continued)

(58) Field of Classification Search
CPC ..... A61M 1/0039; A61B 2017/320072; A61B 2017/320096; A61B 2017/320084;
(Continued)

(56) References Cited

U.S. PATENT DOCUMENTS 4,961,424 A * 10/1990 Kubota ............ A61B 17/22012
601/2
5,478,328 A * 12/1995 Silverman ............... A61M 5/32
604/110
(Continued)

*Primary Examiner* — Jenna Zhang
(74) *Attorney, Agent, or Firm* — Wood, Phillips, Katz, Clark & Mortimer

(57) ABSTRACT

Apparatus and methods for phacoemulsification combine a phacoemulsification needle having an offset feature with a handpiece capable of producing longitudinal motion to create a hybrid phacoemulsification effect that is more efficient than conventional longitudinal handpiece-needle combinations and has been demonstrated under certain conditions to be more efficient than needles used with handpieces providing torsional motion. The phacoemulsification needle is of the type having a hollow passageway that terminates in a straight needle tip formed off-axis from the passageway, allowing the needle tip to move eccentrically when the needle is subjected to torsional or longitudinal vibratory motion. The tip may be flared or may be coextensive with the needle body. The tip may also be angled with respect to the needle body. The aspiration passageway formed through the needle body may be positioned or shaped to be off-axis from the needle body axis.

7 Claims, 12 Drawing Sheets

Related U.S. Application Data

(60) Provisional application No. 61/155,145, filed on Feb. 24, 2009, provisional application No. 61/154,763, filed on Feb. 23, 2009, provisional application No. 61/152,622, filed on Feb. 13, 2009.

(51) Int. Cl.
*A61B 17/3205* (2006.01)
*A61M 1/00* (2006.01)

(52) U.S. Cl.
CPC ............ *A61B 2017/320072* (2013.01); *A61B 2017/320098* (2017.08)

(58) Field of Classification Search
CPC ......... A61B 17/320068; A61F 9/00745; A61F 9/00736; A61F 9/00763; A61F 9/007
See application file for complete search history.

(56) References Cited

U.S. PATENT DOCUMENTS

| | | | | |
|---|---|---|---|---|
| 5,676,649 A | * | 10/1997 | Boukhny | A61F 9/00745 604/22 |
| 5,725,495 A | * | 3/1998 | Strukel | A61M 1/0043 604/22 |
| 5,741,226 A | * | 4/1998 | Strukel | A61M 1/0035 604/22 |
| 5,743,871 A | * | 4/1998 | Strukel | A61M 1/0043 604/22 |
| 5,993,408 A | * | 11/1999 | Zaleski | A61F 9/00745 604/22 |
| 6,007,513 A | * | 12/1999 | Anis | A61F 9/00763 604/22 |
| 6,007,555 A | * | 12/1999 | Devine | A61F 9/00745 604/22 |
| 6,165,150 A | * | 12/2000 | Banko | A61F 9/00745 604/22 |
| 6,402,769 B1 | * | 6/2002 | Boukhny | B06B 1/0611 606/169 |
| 6,533,750 B2 | * | 3/2003 | Sutton | A61F 9/00745 604/187 |
| 8,764,782 B2 | * | 7/2014 | Akahoshi | A61F 9/00745 604/22 |
| 8,801,737 B2 | * | 8/2014 | Akahoshi | A61F 9/00745 604/22 |
| 2002/0099325 A1 | * | 7/2002 | Sutton | A61F 9/00745 604/22 |
| 2002/0099328 A1 | * | 7/2002 | Scheiner | A61N 1/30 604/67 |
| 2004/0193121 A1 | * | 9/2004 | Kadziauskas | A61F 9/00745 604/272 |
| 2004/0199192 A1 | * | 10/2004 | Akahoshi | A61F 9/00745 606/169 |
| 2006/0052758 A1 | * | 3/2006 | Dewey | A61F 9/00745 604/272 |
| 2007/0249942 A1 | * | 10/2007 | Salehi | A61F 9/00745 600/471 |
| 2007/0260199 A1 | * | 11/2007 | Rockley | A61F 9/00745 604/272 |
| 2008/0058708 A1 | * | 3/2008 | Akahoshi | A61F 9/00745 604/22 |
| 2008/0281277 A1 | * | 11/2008 | Thyzel | A61F 9/007 604/256 |
| 2008/0294087 A1 | * | 11/2008 | Steen | A61F 9/00745 604/22 |
| 2009/0143795 A1 | * | 6/2009 | Robertson | A61B 17/320092 606/169 |
| 2010/0010419 A1 | * | 1/2010 | Akahoshi | A61F 9/00745 604/22 |
| 2011/0015561 A1 | * | 1/2011 | Akahoshi | A61F 9/00763 604/22 |
| 2011/0046541 A1 | * | 2/2011 | Akahoshi | A61F 9/00745 604/22 |
| 2011/0166502 A1 | * | 7/2011 | Nallakrishnan | A61F 9/00745 604/22 |
| 2011/0172588 A1 | * | 7/2011 | Akahoshi | A61F 9/00745 604/22 |
| 2012/0197215 A1 | * | 8/2012 | Akahoshi | A61F 9/00736 604/272 |
| 2013/0096569 A1 | * | 4/2013 | Akahoshi | A61F 9/00745 606/107 |
| 2013/0237993 A1 | * | 9/2013 | Nallakrishnan | A61F 9/00745 606/107 |
| 2014/0249538 A1 | * | 9/2014 | Akahoshi | A61F 9/00763 606/107 |
| 2014/0330283 A1 | * | 11/2014 | Nallakrishnan | A61F 9/00736 606/107 |
| 2015/0173950 A1 | * | 6/2015 | Nallakrishnan | A61F 9/00745 604/22 |
| 2017/0042732 A1 | * | 2/2017 | Akahoshi | A61F 9/00745 |

* cited by examiner

APPARATUS AND METHOD FOR PHACOEMULSIFICATION

This application is a continuation based on U.S. patent application Ser. No. 12/408,715, which claims priority from U.S. Provisional Patent Application Ser. No. 61/152,622, filed Feb. 13, 2009, Ser. No. 61/154,763, filed Feb. 23, 2009, and Ser. No. 61/155,145, filed Feb. 24, 2009, all of which are incorporated herein, by reference, in their entirety.

FIELD OF THE INVENTION

This disclosure relates to surgical instruments and surgical techniques used in eye surgery and more particularly, to phacoemulsification apparatuses and methods for their use.

BACKGROUND OF THE INVENTION

A common ophthalmological surgical technique is the removal of a diseased or injured lens from the eye. Earlier techniques used for the removal of the lens typically required a substantial incision to be made in the capsular bag in which the lens is encased. Such incisions were often on the order of 12 mm in length.

Later techniques focused on removing diseased lenses and inserting replacement artificial lenses through as small an incision as possible. For example, it is now a common technique to take an artificial intraocular lens (IOL), fold it and insert the folded lens through the incision, allowing the lens to unfold when it is properly positioned within the capsular bag. Similarly, efforts have been made to accomplish the removal of the diseased lens through an equally small incision.

One such removal technique is known as phacoemulsification. A typical phacoemulsification tool includes a handpiece to which is attached a hollow needle. Electrical energy is applied to a piezoelectric crystal to vibrate the needle at ultrasonic frequencies in order to fragment the diseased lens into small enough particles to be aspirated from the eye through the hollow needle. Commonly, an infusion sleeve is mounted around the needle to supply irrigating liquids to the eye in order to aid in flushing and aspirating the lens particles.

It is extremely important to properly infuse liquid during such surgery. Maintaining a sufficient amount of liquid prevents collapse of certain tissues within the eye and attendant injury or damage to delicate eye structures. As an example, endothelial cells can easily be damaged during such collapse and this damage is permanent because these cells do not regenerate. Some benefits of using as small incision as possible during such surgery are the minimization of leakage of liquid during and after surgery to help prevent tissue collapse, faster healing time and decreased post-operative astigmatism.

Phacoemulsification needles and tips are well represented in the prior art. Needles and tips of varying configurations are well known. A particular shape for a tip or needle is often dictated by the type of handpiece with which the needle is to be used.

U.S. Pat. No. 5,725,495 (Strukel et al.) teaches and describes a phacoemulsification handpiece, sleeve and tip illustrating a wide variety of tip configurations and needle cross-sectional configurations.

U.S. Pat. No. 6,007,555 (Devine) teaches and describes an ultrasonic needle for surgical emulsification. The needle and its tip are shown in both circular and oval configurations.

U.S. Pat. No. 6,605,054 (Rockley) teaches and describes a multiple bypass port phacoemulsification tip having multiple aspiration ports and a single discharge port to infuse liquid into the eye.

U.S. Pat. No. 5,879,356 (Geuder) teaches and describes a surgical instrument for crushing crystalline eye lenses by means of ultrasound and for removing lens debris by suction which demonstrates the use of a sleeve positioned concentric to the needle and having a pair of discharge ports formed thereon.

U.S. Pat. No. 5,645,530 (Boukhny) teaches and describes a phacoemulsification sleeve, one variation of which has a bellows portion attached to a discharge port ring which directs an annular flow of liquid around the needle and into the eye. The use of the bellows is intended to allow the sleeve to absorb spikes in liquid pressure during the operation.

Published U.S. Patent Application No. 2003/0004455 (Kadziauskas) teaches and describes a bi-manual phacoemulsification needle using separate emulsification and aspiration needles inserted into the eye simultaneously during surgery.

Published U.S. Patent Application No. 2006/0217672 (Chon) teaches and describes a phacoemulsification tip that is swaged or crimped at its distal end. The tip is intended for use with a handpiece producing torsional motion and the crimping forms cutting edges at the distal end.

Many phacoemulsification needles and tips are designed for use with handpieces that vibrate the needle longitudinally at relatively low frequencies. In addition to longitudinal vibration, certain handpieces sold by Alcon, Inc. of Ft. Worth, Tex. claim to impart a torsional motion to the needle at an oscillation vibration frequency of about 100 cycles/second. There are also handpieces that provide torsional oscillation of the phacoemulsification tip at frequencies of about 32,000 cycles/second.

Use of the torsional-type handpiece has called for phacoemulsification needle tip designs differing from those used with the longitudinal-type handpiece. For example, needles have been designed with tips that are shaped, swaged and angled to take advantage of the needle motion created by the handpiece.

Many surgeons favor phacoemulsification needles having the straight tip design commonly used with longitudinal hand pieces. The great majority of surgeons use longitudinal handpieces rather than torsional handpieces, often because torsional phacoemulsification equipment is more expensive than longitudinal equipment, and thus find themselves unable to take advantage of the enhanced phacoemulsification results claimed in torsional phaco.

Forming a needle tip in an off-axis position relative to the axis of the aspiration passageway extending through the needle body causes eccentric motion or "wobble" during torsional phacoemulsification and improves the efficiency of phacoemulsification while retaining the straight-tip configuration. Surprisingly, I have also found that forming the tip in such an off-axis position also increases the efficiency of phacoemulsification when using a longitudinal handpiece. Preliminary clinical examinations indicate that using an off-axis needle with a longitudinal handpiece may be more efficient than using the same needle with a torsional handpiece providing 100% torsional action, where efficiency is measured by the energy dissipated during phacoemulsification. When used herein, the term "dissipated energy" refers to the amount of energy, most commonly measured in joules, used by the hand piece during phacoemulsification. Lower dissipated energy readings mean that less heat is being produced during phacoemulsification which lowers the possibility of thermal damage to the delicate eye tissues.

There are known phacoemulsification apparatus, such as the Infiniti® Vision System manufactured by Alcon Laboratories of Ft. Worth, Tex. which allow the surgeon to choose between using torsional motion, longitudinal motion, or a blend thereof in a single handpiece. A common blended setting uses torsional motion two-thirds of the time, and longitudinal motion one-third of the time. It is believed that the "blended" motion produces a more three-dimensional effect because of the back-and-forth motion imparted during longitudinal phacoemulsification and the eccentric motion produced at the tip during torsional phaco.

Use of an off-axis tip with a longitudinal handpiece appears to create a hybrid type of phacoemulsification motion without using the more complex and expensive torsional phacoemulsification apparatus. We have also determined that the eccentric or wobble type of motion can be imparted to a phacoemulsification needle with no flare at the tip by forming the central aspiration passageway within the needle body in an off-axis position. It is also expected that similar results will be obtained using a straight phacoemulsification needle having an aspiration passageway that is formed with a cross sectional configuration different than the cross-section configuration of the needle body itself, and that these results will be further amplified if the passageway is also placed off axis.

While the following describes a preferred embodiment or embodiments of the present invention, it is to be understood that such description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

In accordance with a preferred embodiment of the invention a method for phacoemulsification is described wherein a phacoemulsification needle having an off-axis configuration to produce eccentric motion is provided for use with a phacoemulsification handpiece that produces longitudinal motion. The needle has a straight needle tip with a flared tip formed off-axis with respect to the hollow passage formed through the needle.

In a second embodiment the flared tip is angled with respect to the needle body.

In another embodiment the needle tip is unflared and the aspiration passageway is formed offset from the needle body central axis.

In another embodiment the needle tip is unflared and the aspiration passageway has a cross-sectional shape different from that of the needle body.

In another embodiment the needle tip is unflared and the aspiration passageway has a cross-sectional shape different from that of the needle body and is formed offset from the needle body central axis.

BRIEF DESCRIPTION OF THE DRAWINGS

Further aspects of the present invention will be best understood by reference to the accompanying drawings in which like numbers are used to identify like parts, and which are presented to illustrate the aspects of the invention although not necessarily to actual scale, wherein.

DETAILED DESCRIPTION OF THE INVENTION

Figure 1:
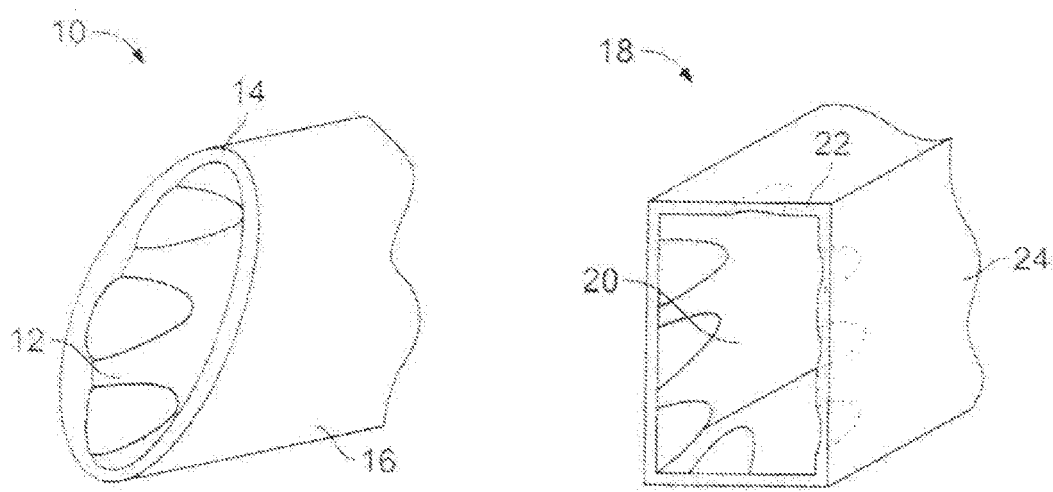
FIG. 1 is a drawing showing prior art straight oval- and square-shaped tips.

Referring now to FIG. 1, the numeral 10 indicates generally a prior art phacoemulsification needle tip as shown in U.S. Pat. No. 6,007,555 (Devine), entitled "Ultrasonic Needle for Surgical Emulsification", issued Dec. 28, 1999. Needle 10 is straight and terminates in an unflared mouth 12 defined by a lip 14 at the end of needle body 16, with lip 14 and needle body 16 formed as having an oval cross-section configuration.

Referring to FIG. 1, the numeral 18 indicates generally a prior art straight, unflared phacoemulsification needle tip from U.S. Pat. No. 6,007,555, having a mouth 20 defined by a lip 22 at the end of needle 24. The cross-sectional configuration of needle 18 and mouth 20 is a rectangle.

Figure 2:
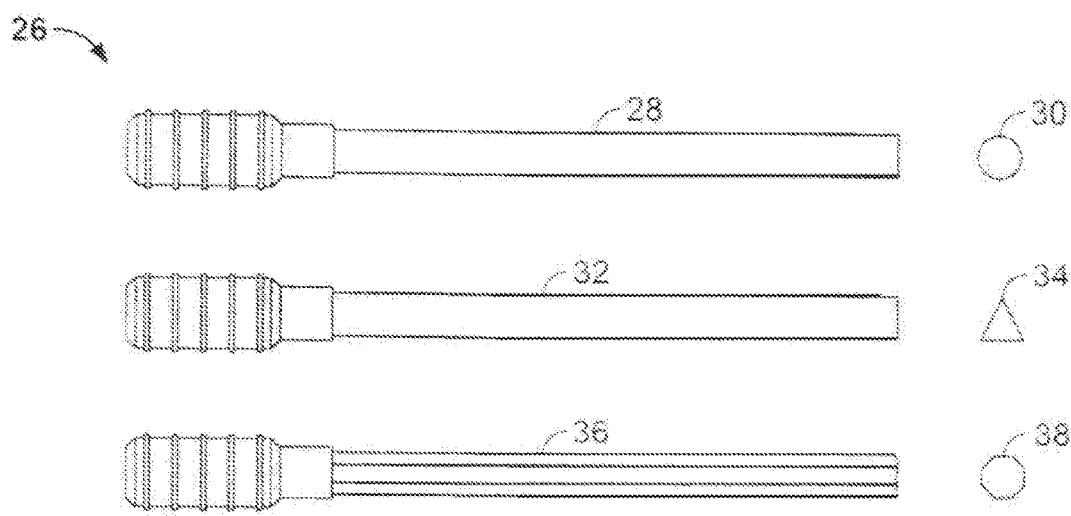
FIG. 2 is a drawing showing several prior art needle cross-sectional configurations.

Referring now to FIG. 2, the numeral 26 identifies several prior art straight phacoemulsification needles as described in U.S. Pat. No. 5,725,495, with needle 28 having a circular cross-section as shown at 30, needle 32 having a triangular cross-section as shown at 34 and needle 36 having an octagonal cross-section as shown at 38. As seen at 30, 34, and 38 of FIG. 2, needles 28, 32, and 36 have exterior shapes or cross-sections identical to the shape and cross-section of the aspiration passageways formed therethrough.

Both tips 10 and 18 in FIG. 1 exemplify one form of a "straight" needle tip, that is, a tip that is coaxial with or centered on the hollow aspiration passageway formed through the needle body and which have no flare or enlargement at the tip. Other straight tips are known which have needle tips that are flared, or larger in cross-sectional area than the needle's aspiration passageway yet which are centered on the passageway.

Phacoemulsification needles are sometimes referred to as "tips". Our use of the term "tip" throughout refers to that end of the needle intended to be inserted into the eye. The remaining portion of the phacoemulsification needle will generally be referred to as the needle body.

Figure 3:
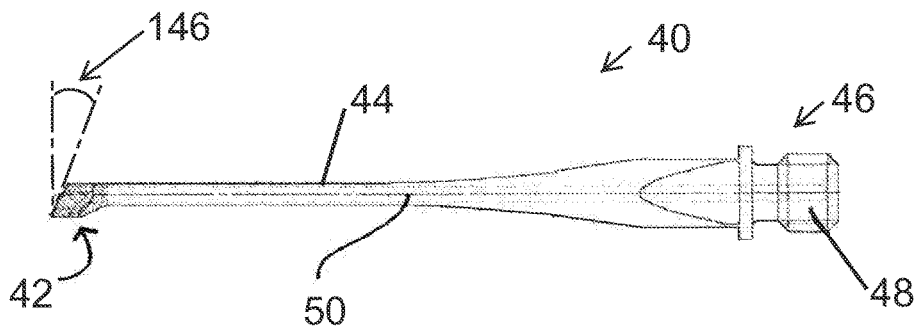
FIG. 3 is a side elevation view of a phacoemulsification needle embodying the present invention.

Referring now to FIG. 3, the numeral 40 indicates generally a phacoemulsification needle having a flared needle tip 42 larger in cross-section than and formed integrally with a distal end of a hollow needle body 44. At a proximal end 46 thereof, needle body 44 terminates in a mount 48 which allows needle 40 to be attached to a phacoemulsification handpiece. Commonly, the mount 48 is threaded and screws onto a phacoemulsification handpiece. In FIG. 3, needle body 44 has a circular cross-section with a longitudinally-extending central axis 50.

Figure 5:
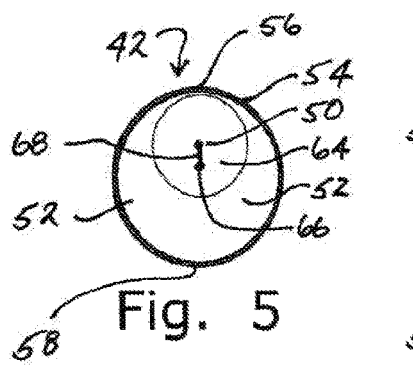
FIG. 5 is a front elevation view of the needle of FIG. 4.

Referring now to FIG. 5, needle 40 is shown in a partial, front elevation view, illustrating the communication of aspiration passageway 64 with tip 42.

Figure 4:
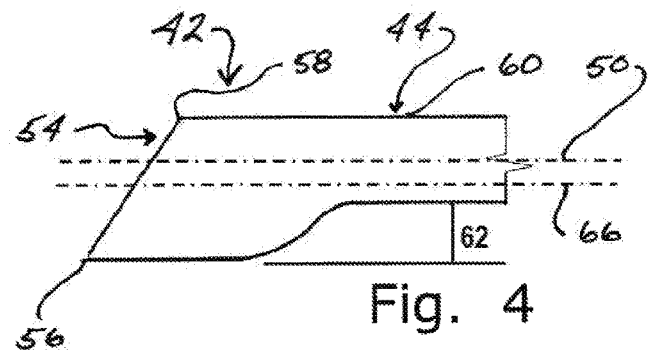
FIG. 4 is a partial side elevation view of the needle of FIG. 3.
Figure 6:
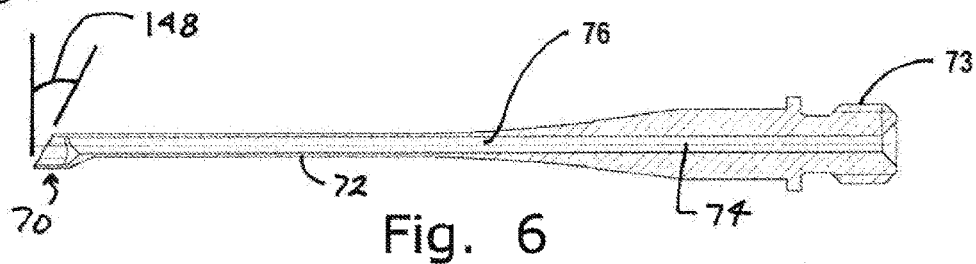
FIG. 6 is a cross-sectional side elevation view of the needle of FIG. 3.

Referring now to FIG. 4, an enlarged partial side elevation view of tip 42 is shown. As seen in both FIGS. 5 and 6, tip 42 has a mouth 52 defined by a lip 54 which, as shown in FIG. 3, is formed at an angle 146 to a plane perpendicular to axis 50. The angle shown is one of choice: lip 54 can also be formed perpendicular to axis 50 or formed in any number of other configurations corresponding generally to the configurations of known straight tips presently used with longitudinally-vibrating handpieces.

As viewed in FIG. 4, tip 42 has a lead portion 56 and a trailing portion 58, with lead portion 56 being that part of lip 54 that extends longitudinally forward past trailing portion 58, while trailing portion 58 is that part of lip 54 that extends the least distance forward. In the embodiment of the needle 40 shown in FIG. 4, trailing portion 58 is substantially co-linear with the outer surface 60 of needle body 44, while lead portion 56 is offset by a distance 62 from the outer surface 60 of needle body 44. The effect of forming lip 54 at the angle shown is to place lead portion 56 at the farthest point from needle body axis 50.

Referring now to FIG. 5, an aspiration passageway 64 of needle body 44 is shown centered on axis 50. Tip mouth 52 is shown defined by lip 54 with lead point 56 and trailing point 58. In the example shown, tip 42 has its own tip axis 66 extending therethrough. As seen in FIGS. 4 and 5, in this example, axes 50 and 66 do not coincide but are offset by a distance 68. As also seen in FIG. 5, the cross-sectional area of tip 42 is larger than the cross-sectional area of needle body 44 when viewed in a plane perpendicular to axis 50.

In a preferred embodiment of the needle 40, the needle body 44 is 1.0 mm in exterior diameter with a wall thickness of 0.10 mm, leaving an interior diameter of 0.80 mm. Tip 42 has an exterior diameter of 1.10 mm and a wall thickness of 0.10 mm. The lateral distance from the point at which tip 42 begins to enlarge outward from needle body 44 to lead point 56 is 1.80 mm, while offset distance 62 is 0.30 mm.

Figure 8:
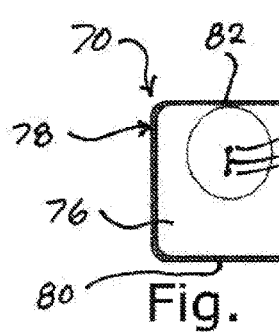
FIG. 8 is a front elevation view of the needle of FIG. 7.
Figure 7:
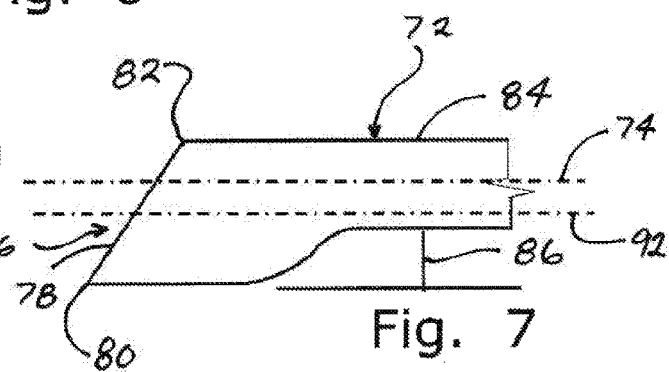
FIG. 7 is a partial side elevation view of a needle having a square tip cross-section.

Referring now to FIGS. 7 and 8, a second embodiment of a needle according to the present invention having a tip 70 with a square in cross-sectional shape and formed integrally with a hollow needle body 72. In the example shown, needle body 72 has a circular cross-section with a longitudinally-extending central axis 74.

Referring to FIG. 7, an enlarged partial side elevation view of the tip 70 is shown. As seen in both FIGS. 7 and 8, tip 70 has a mouth defined by a lip 78 which, in the example shown in FIG. 7, is formed at an angle to axis 74. The angle shown is one of choice: lip 78 can also be formed perpendicular to axis 74 or any number of other configurations corresponding generally to the configurations of known straight tips presently used with longitudinally vibrating hand pieces.

As viewed in FIG. 7, tip 70 has a lead lip portion 80 and a trailing lip portion 82, with lead portion 80 being that part of lip 78 that extends longitudinally past trailing portion 82, while trailing portion 82 is that part of lip 78 that extends the least distance longitudinally forward. In the example shown in FIG. 7, trailing lip portion 82 is substantially co-linear with the outer surface 84 of needle body 72, while lead lip portion 80 is offset by a distance 86 from the outer surface 84 of needle body 72. The effect of forming lip 78 at an angle is to place lead lip portion 80 farthest from needle body axis 74.

Referring now to FIG. 8, the front elevation view of the tip 70 is shown. Needle body 72 (not illustrated in FIG. 8) has a central aspiration passageway 76 extending therethrough, centered on axis 74. In the example shown, tip 70 has its own central axis 92, which, as seen in FIGS. 7 and 8 is offset from needle body axis 74 by a distance 90. As also seen in FIG. 8, the cross-sectional area of tip 70 is greater than the cross-sectional area of needle body 72 when viewed in a plane perpendicular to axis 74.

Figure 9:
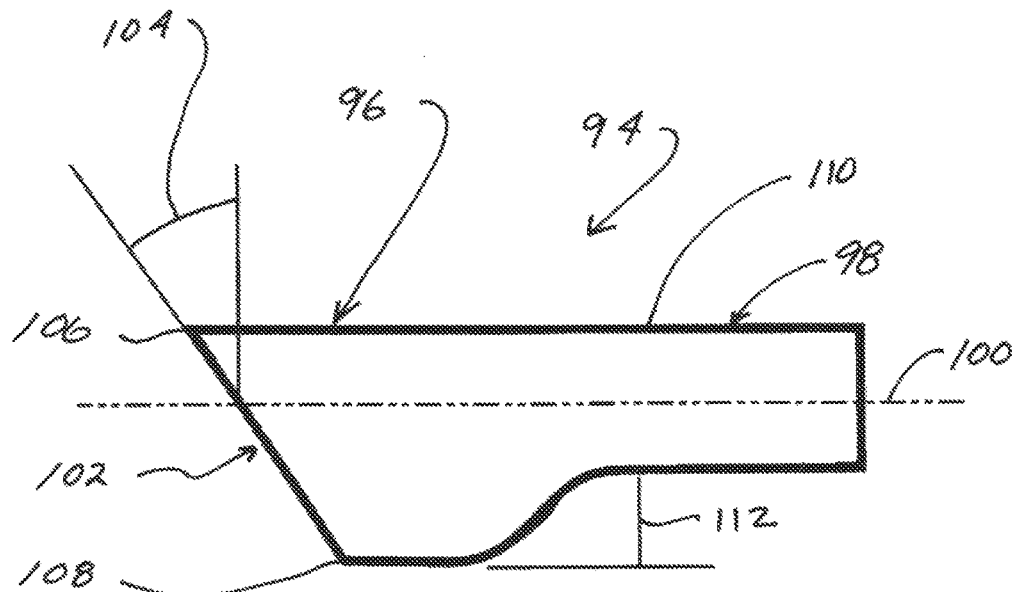
FIG. 9 is a partial side elevation view of a variation of the needle shown in FIG. 4.

Referring now to FIG. 9 the numeral 94 identifies another embodiment of a phacoemulsification needle of the present invention constructed substantially as described with respect to FIGS. 3, 4, 5 and 6. Needle 94 has a tip 96 formed with a circular cross-section and integral with needle body 98. Needle body 98 has a central axis 100.

Tip 96 has a square mouth 102 which, in this example, is formed at an angle 104 to a plane normal to axis 100. In this example, angle 104 is measured 30° in a direction opposite to that of angle of mouth 52 as shown in FIG. 3. This angle 104 is a matter of choice and other angles can be used as well. In this configuration, tip 96 has a lead point 106 and a trailing point 108, corresponding in description to points 56, 58 described above. In this example, lead point 106 is collinear with outer surface 110 of needle body 98 while trailing point 108 is offset from outer surface 110 by a distance 112.

Figure 10:
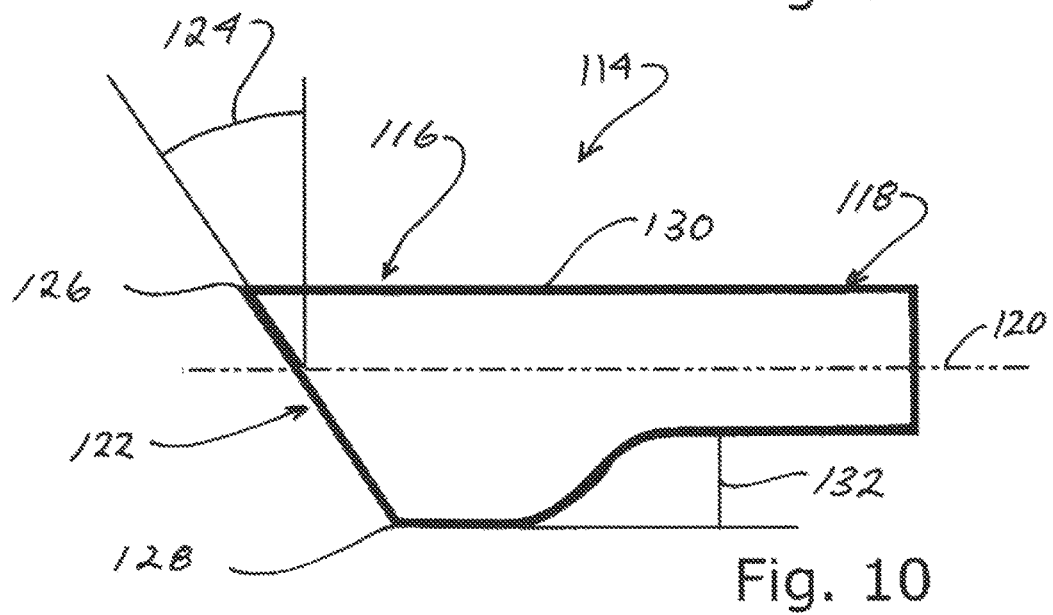
FIG. 10 is a partial side elevation view of a variation of the needle shown in FIG. 7.

Referring now to FIG. 10 the numeral 114 identifies a phacoemulsification needle constructed substantially as described with respect to FIGS. 7 and 8. Needle 114 has a tip 116 formed with a square cross-section and integral with needle body 118. Needle body 118 has a central axis 120.

Tip 116 has a square mouth 122 which, in this example, is formed at an angle 124 to a plane normal to axis 120. In this example, angle 124 is measured 30° in a direction opposite to that of angle of mouth as shown in FIG. 7. In this configuration, tip 116 has a lead lip portion 126 and a trailing lip portion 128, corresponding in description to lip portions 80, 82 described above. In this example, lead lip portion 126 includes a portion of outer surface 130 of needle body 118 while trailing lip portion 128 is offset from outer surface 130 by a distance 132.

Figure 11:
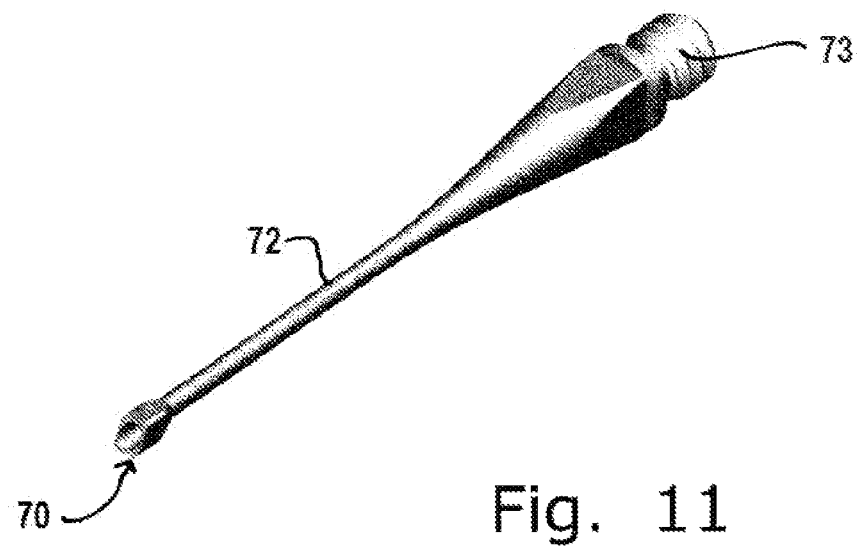
FIG. 11 is a perspective view of the needle of FIG. 7.
Figure 12:
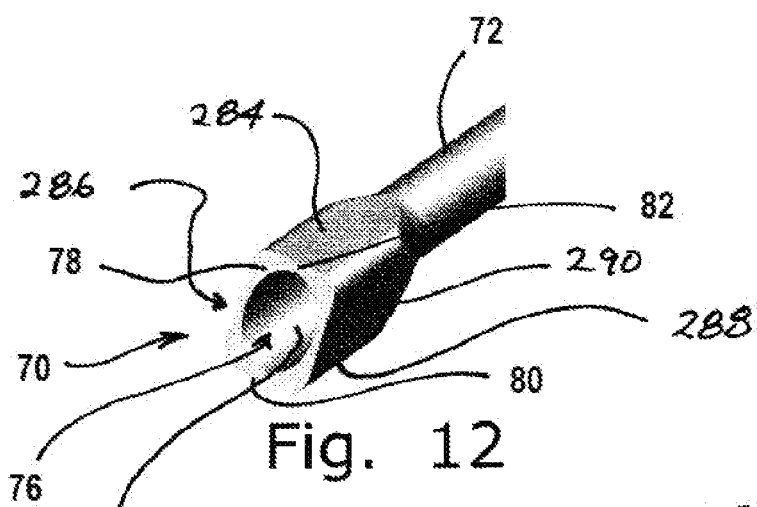
FIG. 12 is an enlarged, partial perspective view of the needle of FIG. 11.
Figure 13:
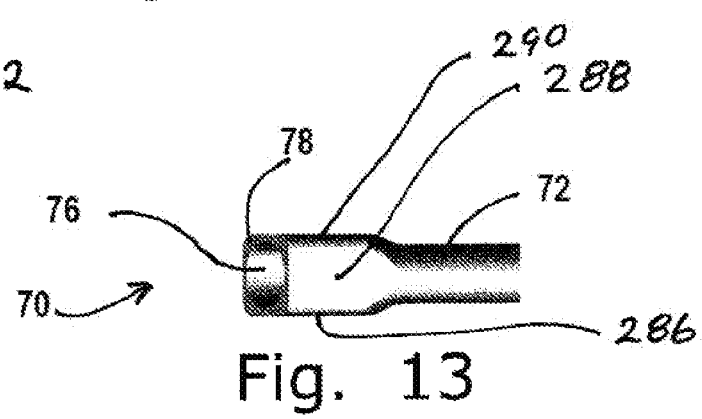
FIG. 13 is an enlarged, partial bottom perspective view of the needle of FIG. 11.

Referring now to FIG. 11, is a perspective view of the needle shown in FIG. 7, with needle body 72 terminating at one end at tip 70 and at the other end at threaded mount 73. FIG. 12 is an enlarged perspective view of tip 70 showing the square configuration of lip 78, leading and trailing portions 80, 82. FIG. 13 is a bottom view of tip 70 showing lip 78 and needle body 72.

Figure 14:
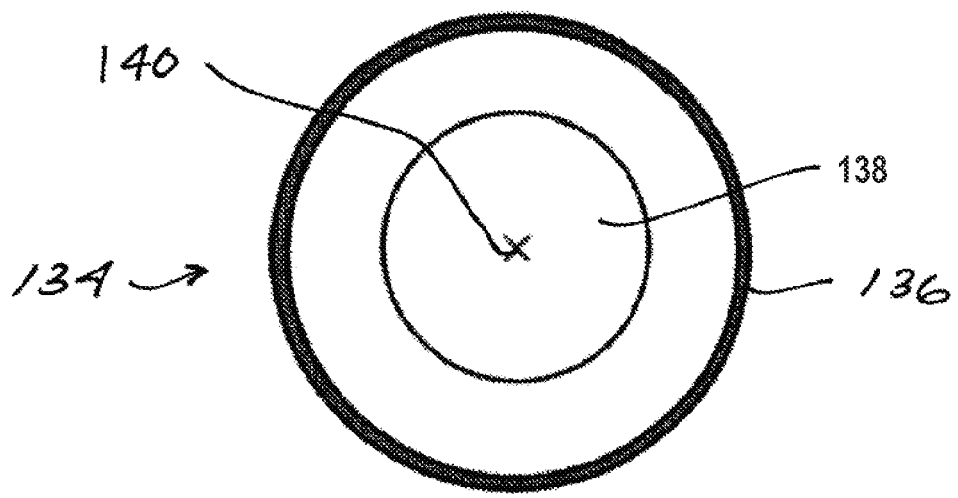
FIG. 14 is a simplified diagrammatic front elevation view of a prior art straight needle tip during torsional motion.
Figure 15:
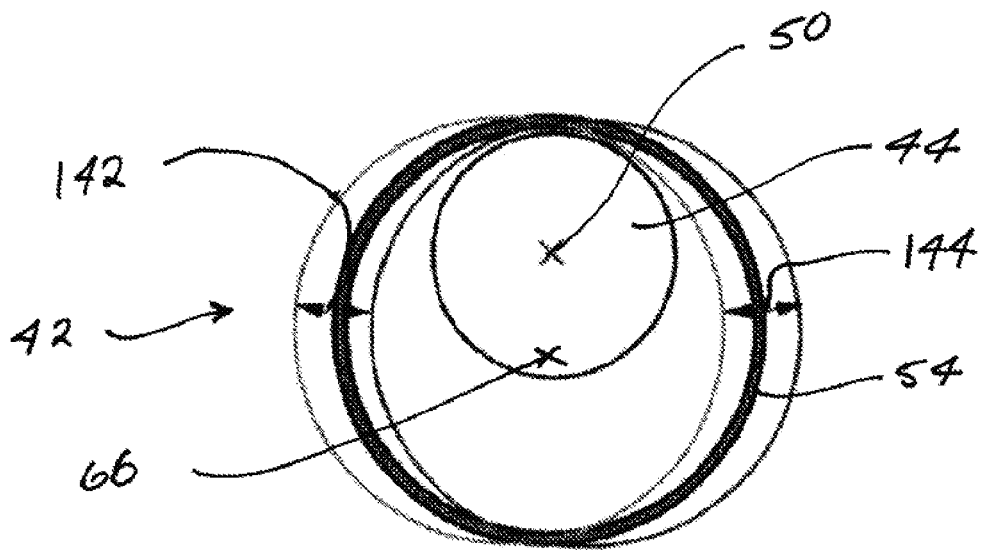
FIG. 15 is simplified diagrammatic front elevation view of a needle tip constructed in accordance with the present invention and used with a torsional or longitudinal handpiece.

The efficacy of having the tip axes in each of the foregoing examples be non-coincident with, or offset from, the needle body axes is demonstrated in FIGS. 14 and 15. Using a needle having a circular tip as an example, the numeral 134 in FIG. 14 identifies a front elevation view of a prior art straight phacoemulsification tip having a circular cross-section defined by mouth 136 integral with and extending from a needle body 138. Hollow needle body 138 has a central, longitudinally-extending axis 140. The geometry of tip 134 is such that axis 140 is also a central, longitudinally-extending axis for tip 134. When needle body 138 with tip 134 is attached to a phacoemulsification handpiece that produces torsional motion about axis 140 the pattern of vibration is generally as shown in FIG. 14, with tip 134 exhibiting little side-to-side or eccentric motion. In other words, lip 136 tends to move in a generally uniform motion about axis 140.

Referring now to FIG. 15, inventive tip 42 of FIG. 5 is shown, with circular lip 54 and needle body 44 having needle body axis 50 and tip axis 66. When tip 42 is subjected to torsional or longitudinal motion, lip 54 moves eccentrically, or "wobbles", in part because the rotation of the tip 42 is not centered on tip axis 66. This produces movement of lip 54 shown by paths 142 and 144, creating an enhanced cutting or emulsifying effect on the tissue contacted by tip 42. Thus, a straight phacoemulsification needle with a flared tip can be used with torsional or longitudinal motion.

The "wobble" effect can be altered by changing the offset distance between the tip axis and the needle body axis, and by changing the geometry of the tip, by using different cross-sectional shapes such as triangular or polygonal.

Figure 16:
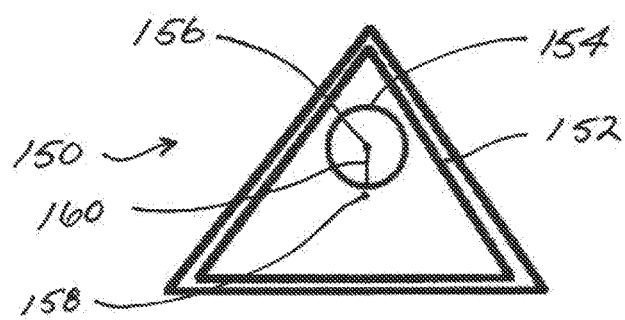
FIG. 16 is a partial front elevation view of a another embodiment of the present invention showing a needle having a triangular offset tip.

Referring now to FIG. 16, the numeral 150 identifies another embodiment of a phacoemulsification tip having a triangular cross-sectional configuration terminating at a lip 152 and communicating with a needle aspiration passageway 154 having an axis 156. Tip 150 has a central tip axis 158 offset from axis 156 by an offset distance 160.

Figure 17:
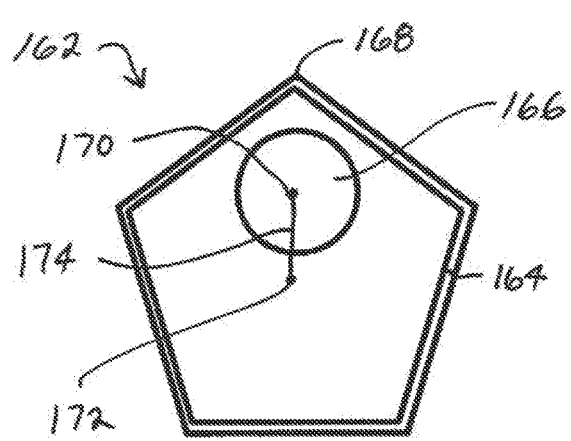
FIG. 17 is a partial front elevation view of a another embodiment of the present invention showing a needle having a pentagonal offset tip with the aspiration passageway formed at an apex to adjacent sides of the pentagon.

Referring now to FIG. 17, the numeral 162 identifies another embodiment of a phacoemulsification tip having a pentagonal cross-section terminating at a lip 164. Tip 162 communicates with a needle aspiration passageway 166 proximate apex 168. Passageway 166 has a central axis 170 and tip 162 has a central axis 172 offset from axis 170 by an offset distance 174.

Figure 18:
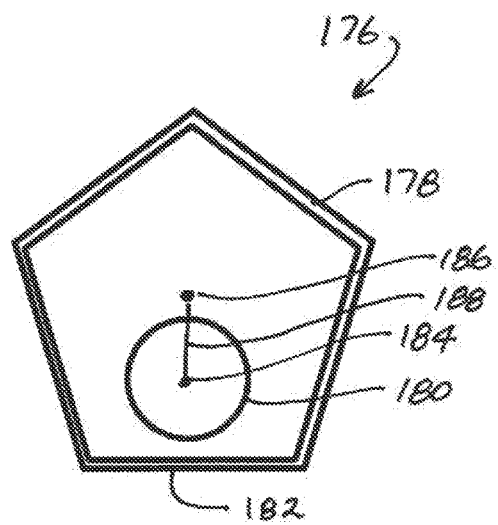
FIG. 18 is a partial front elevation view of a another embodiment of the present invention showing the aspiration passageway positioned along one side of the pentagonal tip.

Referring now to FIG. 18, the numeral 176 identifies another embodiment of a phacoemulsification tip having a pentagonal cross-sectional shape terminating in a lip 178. A needle aspiration passageway 180 extends to tip 176 proximate tip wall 182. Passageway 180 has a central axis 184 while tip 176 has a central axis 186 offset from axis 184 by offset distance 188.

Figure 19:
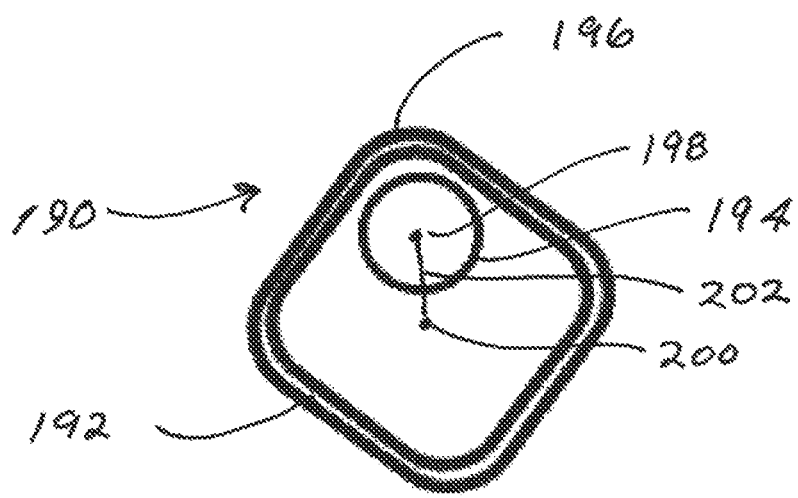
FIG. 19 is a partial front elevation view of a another embodiment of the present invention showing a needle with a square tip having an aspiration passageway positioned at an apex of two adjacent sides of the square tip.

Referring now to FIG. 19, the numeral 190 identifies another embodiment of a phacoemulsification tip having a square cross-sectional shape terminating in a lip 192. A needle aspiration passageway 194 is formed proximate apex 196 of tip 192. Passageway 194 has a central axis 198 while tip 190 has a central axis 200 offset from axis 198 by an offset distance 202.

Phacoemulsification tips may also be formed on needle bodies that are noncircular in cross-section.

Figure 20:
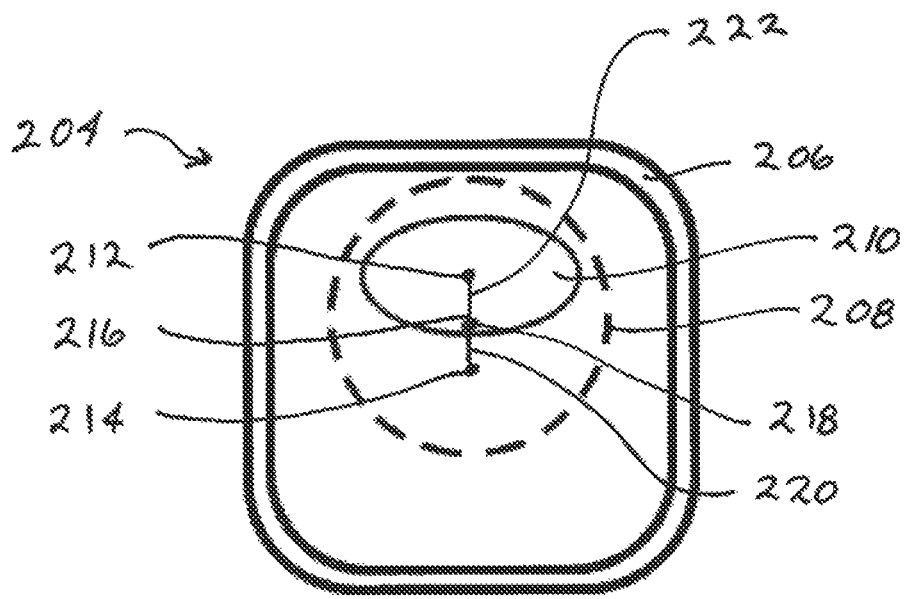
FIG. 20 is a partial front elevation view of a another embodiment of the present invention showing a needle with a square tip extending from a needle body having a circular outer cross-section and an aspiration passageway with an oval cross-section.

Referring now to FIG. 20, the numeral 204 identifies another embodiment of a phacoemulsification tip having a square cross-sectional shape terminating in a lip 206. Tip 204 extends from a needle body 208 having a circular cross-sectional shape. Needle body 208 has an oval-shaped needle aspiration passage 210 having a central axis 212 while tip 204 has a central axis 214 offset from axis 212 by an offset distance 216.

The foregoing examples have shown tips with flared shapes, that is, tips with cross-sectional shapes that are larger in size than the cross sectional shape of the needle body. Similar results are predicted for certain phacoemulsification needles with no flared tip that is the terminus of the needle is the same cross-sectional shape as the needle body.

Figure 21:
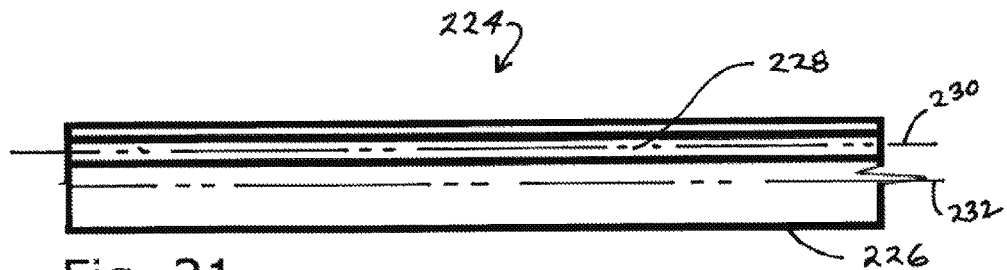
FIG. 21 is a side elevation cross-sectional view of a portion of a straight, unflared phacoemulsification needle having a circular exterior cross-section shape and an internal aspiration passageway having an oval cross-sectional shape.
Figure 22:
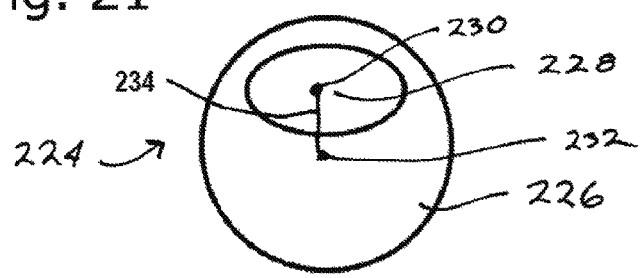
FIG. 22 is a front elevation view of the needle of FIG. 21.

Referring now to FIG. 21, the numeral 224 identifies a straight phacoemulsification needle having a needle body 226 through which an aspiration passageway 228 is formed. As shown in FIG. 22, passageway 228 has an oval cross-sectional shape and has a central axis 230. Needle body 226 has a central axis 232 offset from passageway axis 230 by an offset distance 234.

Figure 23:
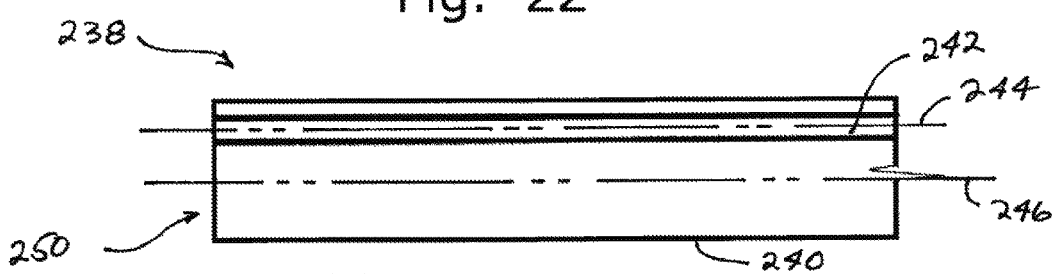
FIG. 23 is a side elevation cross-sectional view of a portion of a straight, unflared phacoemulsification needle having an oval cross-sectional shape with an aspiration passageway having a circular cross-sectional shape and offset toward one end of the needle body.
Figure 24:
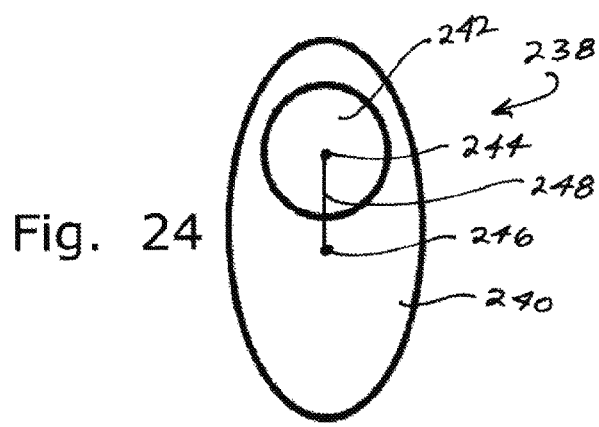
FIG. 24 is a front elevation view of the needle of FIG. 23.

Referring now to FIG. 23, a straight phacoemulsification needle 238 has a needle body 240 formed with an oval cross-section. As shown in FIG. 24 an aspiration passageway 242 is formed through needle body 240 and in the embodiment shown has a circular cross-section. Passageway 242 has a central axis 244 and needle body 240 has a central axis 246 offset from axis 244 by an offset distance 248.

While the needle bodies referred to in the foregoing examples have been referred to as circular in cross-section it should be understood that different cross-sectional shapes can also be used.

The foregoing examples have demonstrated round and square eccentric tips. Other tip cross-sectional shapes can also be used and the tips can be made with various orientations. For example, tip 70 can be rotated around tip axis 92 to create a different orientation. It is expected that the wobble effect will be manifested when the axis of the tip is offset from the axis of the needle body no matter what configuration is used.

Lips such as those shown at 54 and at 78 may also be polished to a smooth finish to add a protective feature. Phacoemulsification efficacy may also be enhanced by roughening a portion of the outer surface of the tips herein detailed.

Offsetting the tip of an angled phacoemulsification needle tip increases efficiency as compared to a symmetrically fashioned tip. Phacoemulsification needles having flared tips that are angled with respect to the needle body are known in the art. Heretofore, such tips have been formed such that the bent portion of the needle body met the flared tip such that the tip was symmetrical about the needle body.

Figure 25:
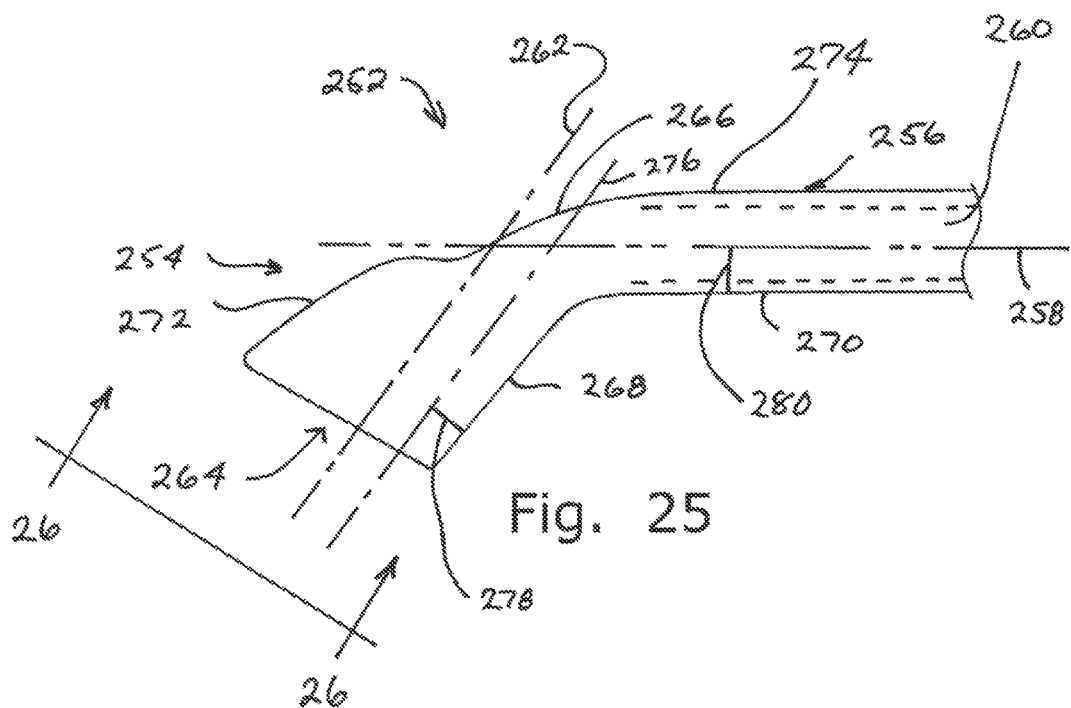
FIG. 25 is a lateral view of another embodiment of a phacoemulsification needle according to the present invention with an angled tip formed off-axis to the needle body.
Figure 26:
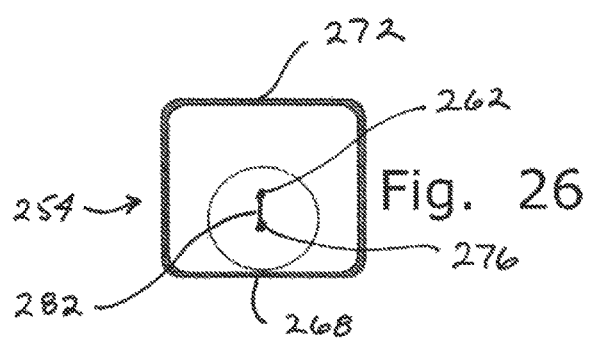
FIG. 26 is a view along plane 26-26 of FIG. 25.

Referring now to FIG. 25 the numeral 252 identifies a portion of another embodiment of an inventive phacoemulsification needle which includes a tip 254 and a needle body 256. Needle body 256 has a longitudinal axis 258 and an aspiration passageway 260 extending along its length. As can be seen in FIGS. 25 and 26, the aspiration passage 260 is circular in shape and is substantially uniform through the length of the needle body 256. Tip 242 has an axis 262 that is centered on the tip opening 264. In this example, the tip 254 has a square cross-section.

A bend 266 is formed on needle body 256 and, as shown in FIG. 25, tip 254 is formed with a first wall portion 268 that is coextensive with bend 266 and first needle body portion 270. Tip 254 has a second wall portion 272 that is offset from bend 266 and needle body portion 274. Secondary needle body axis 276 is shown as positioned the same distance 278 from first wall portion 268 as the distance 280 that axis 258 is positioned from first needle body portion 270.

Referring now to FIG. 26, an end view of tip 254 is shown takes as a view along plane 26-26 of FIG. 25. Axes 262 and 276 are shown to offset one from the other by a distance 282. This offset increases the eccentric motion exhibited by tip 254 and makes phacoemulsification more efficient.

The safety and efficiency of phacoemulsification tips embodying the foregoing aspects of the present invention are enhanced when the inner and outer surfaces of the phacoemulsification tip is roughened, as by sandblasting, and where the lip of the tip mouth is polished to round the lip and remove burrs which can damage delicate tissue in the eye, such as the posterior capsule, which may be contacted by the needle tip during phaco.

The square tip 70 shown in FIGS. 11, 12 and 13 is exemplary of the type of surfaces to which the roughening process is applied.

As seen in FIG. 12, tip 70 has an upper face 284, a left lateral face 286, a lower face 288 and a right lateral face 290.

The identifiers "left" and "right" are used here to designate those faces as seen by one viewing FIG. 12. As can be appreciated, tip 70 has four external faces, all of which are roughened, beginning at and extending away from lip 78.

As further seen in FIG. 12, tip 70 has an inner tip surface 292 extending rearward toward needle body 72 and aspiration passageway (not illustrated). It is a feature of the present invention that the inner tip surface 292 is also roughened, as by sandblasting. The inner and outer surfaces of tip 70 are modified by roughening to create an uneven geometry providing numerous projections which are engaged by the tissue being emulsified as tip 70 is driven in its eccentric, or "wobble" motion.

Figure 27:
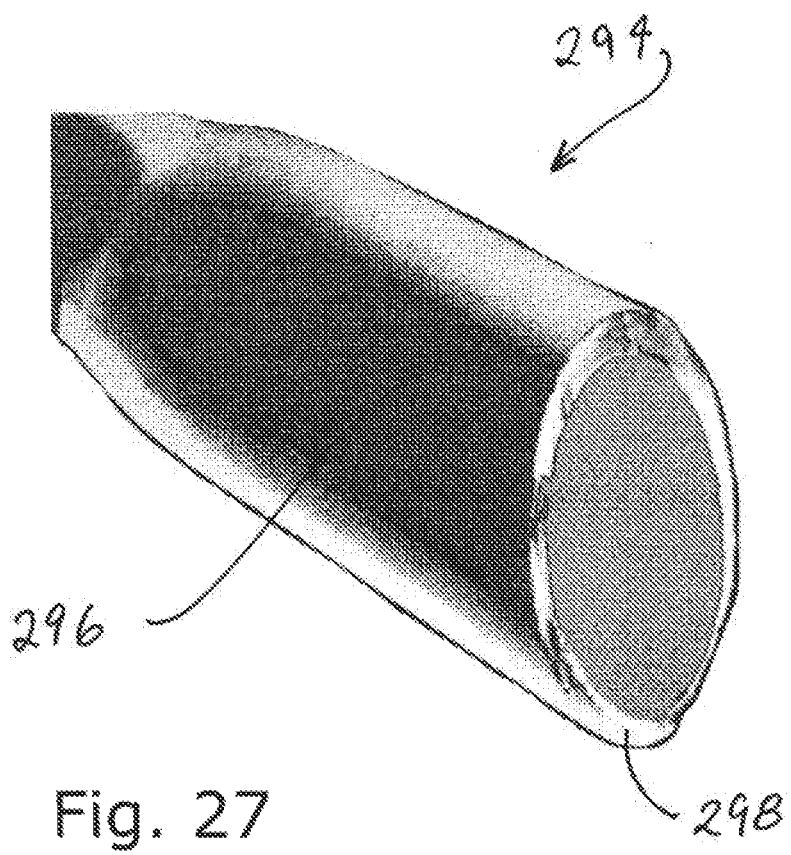
FIG. 27 is an enlarged perspective view of a flared phacoemulsification needle tip.

It is another feature of the present invention to enhance the safety of the tips described herein by highly polishing the lip of each. Referring to FIG. 27 the numeral 294 identifies a phacoemulsification needle having a flared tip 296 terminating at a lip 298. In the example shown, tip 296 has a circular cross-section but the following description applies to the various tips of varying geometry described herein. Tip 296 is intended to be representative of phacoemulsification tips as customarily manufactured. Tip 296 is shown in a magnified view.

Figure 28:
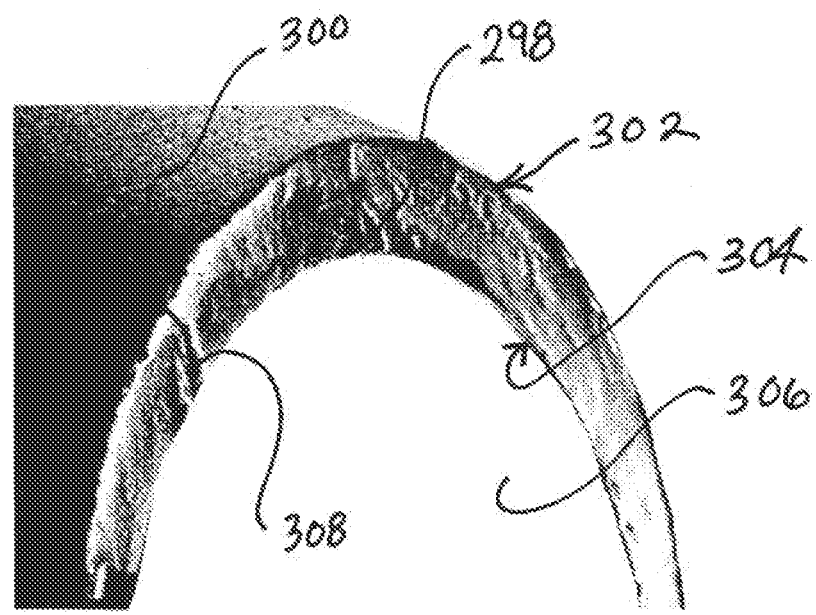
FIG. 28 is an enlarged perspective view of FIG. 27.

A portion of lip 298 is seen in FIG. 28 in a more highly magnified view. The surface 300 of lip 298 is seen to meet tip 296 at substantially a right angle, forming a roughened edge 302. The same configuration creates a roughened edge 304, formed where lip surface 300 and tip inner surface 306 meet. Tip surface 300 is also characterized by upstanding ridges such as those identified by the numeral 308.

Edges 302 and 304, and ridges 308 are somewhat analogous to the "flashing" or "burrs" created when metallic workpieces are cut or severed. Because of the relatively thin metallic material from which phacoemulsification needles are formed, such edges and ridges are themselves thin and sharp, certainly sharp enough to snag corneal tissue when a phacoemulsification needle is inserted through a corneal incision. They are also sharp enough to damage delicate eye tissue, such as the posterior capsule, if the needle tip is brought into contact with the capsule during surgery.

I have determined that a process of rounding and highly polishing and smoothing the lips of phacoemulsification needle tips of the type described herein reduces the likelihood that delicate eye tissue will be damaged during phaco, particularly if the needle is being sued with a handpiece that produces torsional or elliptical motion.

Figure 29:
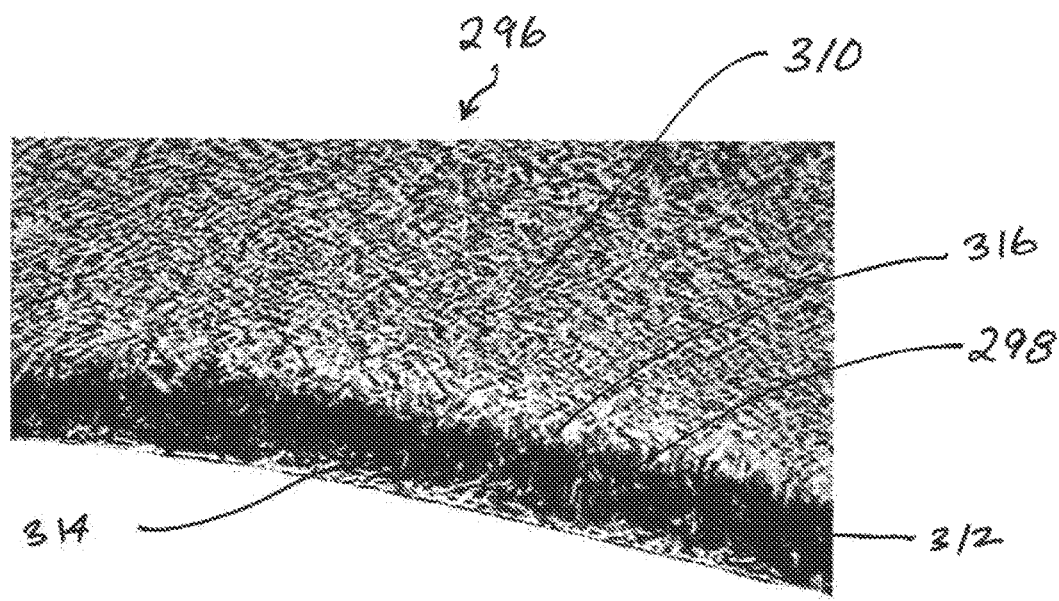
FIG. 29 is a microscopic perspective view of a portion of the outer surface of the needle tip of FIGS. 27 and 28 after roughening and polishing.

Referring now to FIG. 29 the numeral 310 identifies the outer surface of an inventive tip 296 after a roughening procedure has been performed. As can be seen, surface 310 is "pitted" to create a much larger surface area for contact with tissue to be phacoemulsified.

FIG. 29 also shows a portion 312 of lip 298 after polishing. Lip surface 314 now meets outer surface 310 at a rounded edge 316, much smoother and snag-free than the roughened edge 302 shown in FIG. 28.

Figure 30:
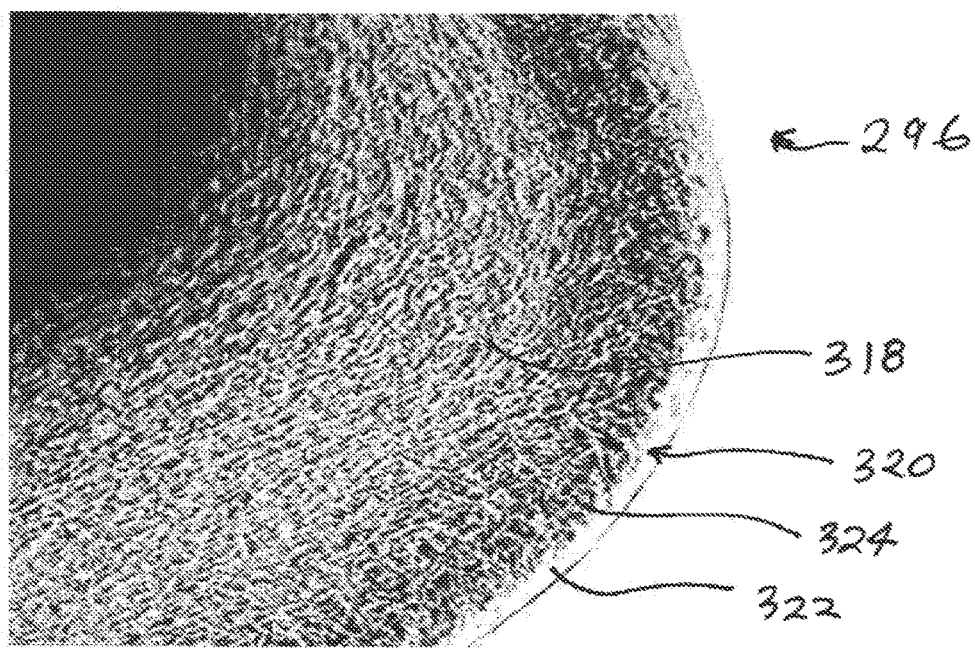
FIG. 30 is a microscopic perspective view of a portion of the inner surface of the tip of FIGS. 27 and 28 after roughening and polishing.

In like fashion, a portion of inner surface 318 of tip 296 is shown after a roughening procedure has been performed. FIG. 30 also shows a portion 320 of lip 298 after polishing. Lip surface 322 now meets inner surface 318 at a rounded edge 324, much smoother and snag-free than the roughened edge 304 shown in FIG. 28.

The elements of surface finish are described by Quality Magazine (http://www.qualitymag.com/Archives/eacd74ce57c3801OVgnVCM100000f932a8cO_) as form, waviness and roughness. These elements, as they are present in the surface finish on the lips of the needles described herein, are rounded and smoothed to a degree sufficient to avoid the snagging of the tip on tissue in the eye, particularly the tissue through which the corneal incision is made and the tissue forming the capsular bag.

While the roughening procedure has been preferably described as sandblasting, other types of operations to create a controlledly roughened surface may also be used. In like fashion, other forms of polishing or smoothing devices and procedures can also be used to satisfactorily prepare the lip of each such phacoemulsification needle tip.

Figure 31:
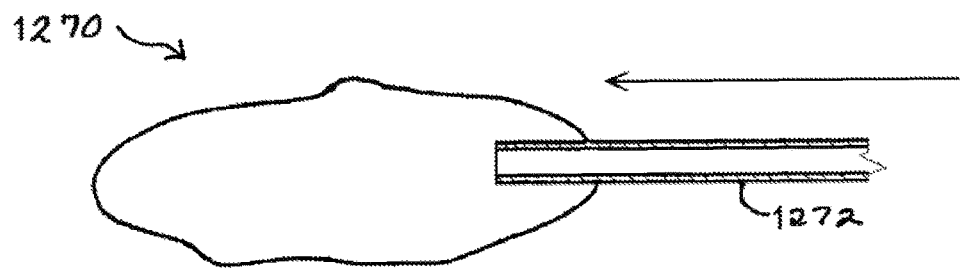
FIG. 31 is a simplified, diagrammatic cross-sectional view of a prior art phacoemulsification needle in contact with a nucleus.
Figure 32:
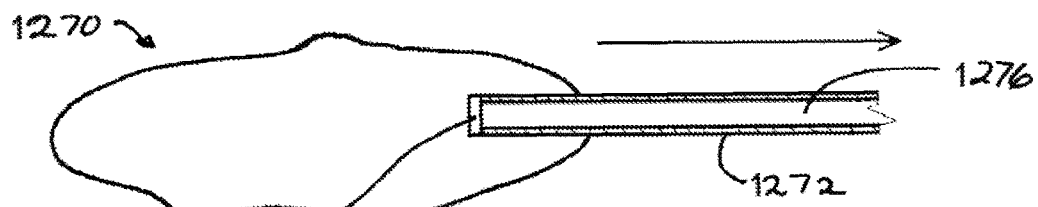
FIG. 32 is view of the needle of FIG. 31 in a moved position.

Referring now to FIGS. 31 and 32, the numeral 1270 identifies generally a lens nucleus undergoing phacoemulsification using a conventional prior art phacoemulsification handpiece imparting only longitudinal motion to a conventional prior art straight phacoemulsification needle 1272. As described previously, in longitudinal phacoemulsification a needle such as 1272 is alternately moved in forward and reverse directions at high speed. Phacoemulsification is more efficient when needle 1272 is in contact with nucleus 1270, particularly with traditional longitudinal phaco, because, as seen in FIG. 31, the cutting of nucleus 1270 occurs when needle 1272 moves forward to contact nucleus 1270. When the needle is drawn in the reverse direction it tends to lose contact with nucleus 1272, creating a gap 1274.

This procedure has several readily noticeable consequences. The forward motion and subsequent contact of needle 1272 with nucleus 1270 can repulse nucleus 1270 and also the fragments into which nucleus 1270 is cut, making more difficult and time-consuming the collection of the fragments through aspiration passageway 1276.

During phaco, a viscoelastic support gel is injected into the lens capsule and the anterior and posterior chambers of the eye. One example of such a gel is Staarvisc® II, manufactured by Staar Surgical Company of Monrovia, Calif. Presence of a gel in the lens capsule helps support and protect the thin walls of the capsule. Using gel in the posterior chamber helps protect the delicate endothelial cells which, if damaged, do not regenerate. During surgery, movement of the gel is readily noticeable when needles such as needle 1272 are vibrating. In particular, it can be seen that the gel present in the posterior chamber of the eye is moved or agitated even though needle 1272 is within the lens capsule.

As a general rule, the longer a phacoemulsification procedure lasts the more energy is expended and the more heat is produced by the ultrasound energy imparted to the needle. More efficient phacoemulsification is accomplished when the lens is fragmented more quickly, the fragmented lens particles are aspirated more quickly and cleanly and less heat is produced. As previously described, one measure of efficiency is the total dissipated energy: less energy is used if the procedure is shorter and one of the ways the procedure can be shortened is to make aspiration more effective. Another measure of efficiency is to observe such occurrences as the uninterrupted aspiration of particles and the "quietness" of the operating environment, meaning the relative lack of turbulence observed in the supporting gel, both in the lens capsule and the posterior chamber. This lack of turbulence can be quite important when, for example, a surgeon is required to use a less than optimal support material, one that may be more susceptible to breakdown during high speed vibration. One such substance is methyl cellulose which is not as viscous or cohesive as a gel such as Staarvisc® II.

Preliminary clinical observations have confirmed that the use of an off-axis phacoemulsification needle with a handpiece producing longitudinal motion results in significantly more efficient phaco. Operation times have been shorter, dissipated energy levels have been lower and the operating environment has been observed to be quieter, with much less agitation of the supporting gel and much less repulsion of the fragmented lens particles. This has resulted in markedly "clear" phacoemulsification results, meaning that the capsule is clearer of unaspirated particles and the supporting gel has provided better protection to the capsule and the endothelial cells.

An ultrasonic handpiece providing longitudinal and torsional motion to a phacoemulsification needle is described in United States Patent Publication 2006/0036180 (Boukhny, et at), entitled "Ultrasonic Handpiece". As the application states, the two modes cannot be activated simultaneously: the handpiece is switchable between the torsional and longitudinal modes. A computer-controlled console allows the surgeon to select alternating time periods for torsional and longitudinal motion, resulting in an effective "blended" motion. The characteristic of such a blended motion are altered when the time periods are altered. For example, a different cutting action and cutting characteristics will result when torsional motion comprises 50 percent of the operating time than when it comprises 75 percent.

A phacoemulsification control system described in United States Patent Publication 2008/0294087 (Steen, et at), assigned to Advanced Medical Optics, Inc. of Santa Ana, Calif. describes a system that imparts a longitudinal motion and lateral motion to the needle by forming the needle with an asymmetric needle mount. Such an arrangement is believed to exhibit certain characteristics of traditional longitudinal phaco, such as the tendency for the needle to lose frontal contact with the nucleus when the needle is moved away from the nucleus, the repulsion of nuclear particles and the tendency to transmit energy to agitate the viscoelastic gel inserted into the eye.

Combining an off-axis tip with a handpiece utilizing longitudinal motion appears to create a hybrid type of tip activity that exhibits some of the characteristics of this blended motion yet exhibits marked improvements in efficiency over systems which utilize modifications to longitudinal handpieces to achieve blended motion.

Use of the present invention can now be described. A phacoemulsification needle having an off-axis construction is mounted to a phacoemulsification handpiece capable of producing longitudinal motion. The geometry of the needle can include needle bodies with centered or off-axis aspiration passageways, needle bodies with centered or off-axis aspiration passageways having different cross-sectional shapes than the needle bodies, with such needles having straight or angled needle tips formed off-axis to the needle body aspiration passageway, with such tips being flared or unflared.

Figure 33:
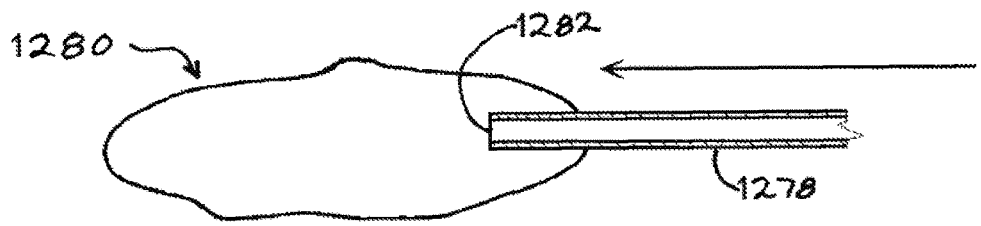
FIG. 33 is a simplified, diagrammatic cross-sectional view of a phacoemulsification needle of the present invention in contact with a nucleus.
Figure 34:
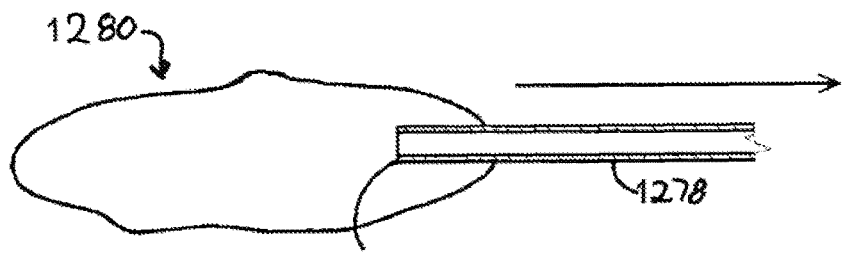
FIG. 34 is view of the needle of FIG. 33 in a moved position.

Referring now to FIGS. 33 and 34 the numeral 1278 identifies a phacoemulsification needle constructed and moved in accordance with the invention described above. FIG. 33 illustrates a straight, unflared needle 1278 as it is being moved in the forward direction during longitudinal motion, showing the tip embedded in nucleus 1280 with the tip mouth 1282 in contact with nucleus 1280. FIG. 34 illustrates needle 1278 in a rearward direction during longitudinal phaco. As seen herein, tip mouth 1282 remains in contact with nucleus 1280. It is believed that the hybrid motion created by combining longitudinal motion of the needle with an off-axis needle or tip allow the aspiration suction to keep tip mouth 1282 in contact with nucleus 1280, greatly reducing repulsion of the nucleus and making aspiration more efficient.

With repulsion reduced the surgeon spends less time "chasing" emulsified lens particles with the tip mouth in order to ultimately aspirate them. Reduced agitation of the gel helps to protect the eye and preserve the field of vision. Phacoemulsification is thus quieter, more efficient and less expensive for the surgeon.

Thus, needles embodying the present invention create a hybrid motion independent of the type of handpiece and control console used. For those instruments designed to create a torsional vibratory motion, needles embodying the present invention create tip motion having a wider cutting range, covering more area. As observed, this hybrid motion appears to exhibit an energy focused more at the tip of the needle surface area, reducing wasted energy. The increase in efficiency exhibited by needles embodying the present invention has been demonstrated by comparing the cumulative dissipated energy levels for a handpiece using both the current and conventional needles to perform the same procedure. Use of the needles disclosed herein results in significantly reduced chatter, repulsion and thermal damage.

It is expected that the principles described herein can also be applied to other surgical instruments as well, such as those used for liposuction and coronary plaque removal. While the present invention has been described in the context of cataract removal, it should be understood that the principles of the present invention can be applied to the removal of different types of tissue as well, such as tumors and the like.

I claim:

1. A phacoemulsification apparatus, said apparatus comprising:
   (a) a handpiece; and
   (b) an elongate needle body having (i) a proximal end terminating at a mount by which said needle body is attached to said handpiece, (ii) a distal end terminating at a tip for emulsifying an internal lens of an eye, and (iii) a body exterior surface between said proximal and distal ends,
   said needle body defining a body central axis,
   said body exterior surface spaced a first distance from said body central axis at a first angular location with respect to said body central axis,
   said needle body having an aspiration passageway extending through said needle body and said tip,
   said tip defining a tip central axis,
   a bend formed on said needle body such that said tip central axis is angled with respect to said body central axis,
   said tip having a first wall portion that is coextensive with said bend and said needle body, said tip having a second wall portion that is offset from said bend and said needle body,
   said tip central axis being spaced from said first wall portion by a second distance at a second angular location, said second distance being greater than said first distance,
   said needle body having a secondary needle body axis that is (i) substantially parallel to and offset from said tip central axis and said first wall portion, and (ii) spaced from said first wall portion by said first distance in a direction perpendicular to said secondary needle body axis, and
   said handpiece configured to vibrate said needle in a longitudinal direction along said body central axis and to move said tip eccentrically.

2. The phacoemulsification apparatus of claim 1 wherein said tip has a generally square cross-section, taken normal to said tip central axis.

3. The phacoemulsification apparatus of claim 1 wherein said needle body has a length along said body central axis, and said aspiration passageway has a substantially uniform size and shape along said length of said needle body.

4. The phacoemulsification apparatus of claim 3 wherein said aspiration passageway has a substantially circular shape.

5. The phacoemulsification apparatus of claim 1 wherein said body exterior surface has a cross-section having a first shape, taken normal to said body central axis, and said needle body has an interior surface defined by said aspiration passageway with a cross-section having a second shape different from said first shape, taken normal to said body central axis.

6. The phacoemulsification apparatus of claim 1 wherein said tip has an interior surface terminating in a lip, and at least one of said tip exterior surface, said tip interior surface, and said lip is roughened.

7. The phacoemulsification apparatus of claim 1 wherein said tip has an interior surface terminating in a lip, and said tip is polished.

* * * * *